(12) United States Patent
Zielke

(10) Patent No.: US 10,362,726 B2
(45) Date of Patent: Jul. 30, 2019

(54) ON-THE-GO SOIL SENSORS AND CONTROL METHODS FOR AGRICULTURAL MACHINES

(71) Applicant: Ag Leader Technology, Ames, IA (US)

(72) Inventor: Roger R. Zielke, Huxley, IA (US)

(73) Assignee: Ag Leader Technology, Inc., Ames, IA (US)

( * ) Notice: Subject to any disclaimer, the term of this patent is extended or adjusted under 35 U.S.C. 154(b) by 2 days.

(21) Appl. No.: 15/717,296

(22) Filed: Sep. 27, 2017

(65) Prior Publication Data

US 2018/0014455 A1 Jan. 18, 2018

Related U.S. Application Data

(62) Division of application No. 14/818,435, filed on Aug. 5, 2015, now Pat. No. 9,801,329, which is a division
(Continued)

(51) Int. Cl.
| | |
|---|---|
| *A01C 7/10* | (2006.01) |
| *A01B 49/06* | (2006.01) |
| *A01B 63/00* | (2006.01) |
| *A01C 21/00* | (2006.01) |
| *A01C 7/20* | (2006.01) |
| *G01K 1/14* | (2006.01) |
| *G01N 19/10* | (2006.01) |

(Continued)

(52) U.S. Cl.
CPC ............... *A01C 7/10* (2013.01); *A01B 27/00* (2013.01); *A01B 49/06* (2013.01); *A01B 63/008* (2013.01); *A01C 5/062* (2013.01); *A01C 5/068* (2013.01); *A01C 7/105* (2013.01); *A01C 7/20* (2013.01); *A01C 7/203* (2013.01); *A01C 21/00* (2013.01); *G01B 7/26* (2013.01); *G01B 11/22* (2013.01); *G01K 1/14* (2013.01); *G01N 19/10* (2013.01); *G01N 21/27* (2013.01); *G01N 27/223* (2013.01); *G01N 33/24* (2013.01); *A01B 63/1115* (2013.01); *G01B 21/18* (2013.01); *Y10S 111/903* (2013.01)

(58) Field of Classification Search
None
See application file for complete search history.

(56) References Cited

U.S. PATENT DOCUMENTS

| | | | |
|---|---|---|---|
| 3,882,383 | A | 5/1975 | Matlin |
| 4,268,824 | A | 5/1981 | Phillips |
| (Continued) | | | |

FOREIGN PATENT DOCUMENTS

| | | |
|---|---|---|
| KR | 10-0740708 | 7/2007 |
| WO | 95/06881 A1 | 3/1995 |

OTHER PUBLICATIONS

Lee Gi Hun—KR 10-0740708—English Translation.
(Continued)

*Primary Examiner* — Kevin P Mahne
(74) *Attorney, Agent, or Firm* — McKee, Voorhees & Sease, PLC

(57) ABSTRACT

An on-the-go monitor and control means and method for an agriculture machines includes on-the-go soil sensors that can be used to control tillage and seeding depth. On seeder implements, the sensors provide information that affects uniform plant emergence.

6 Claims, 13 Drawing Sheets

Related U.S. Application Data of application No. 13/858,681, filed on Apr. 8, 2013, now Pat. No. 9,629,304.

(51) Int. Cl.

| | |
|---|---|
| *G01N 33/24* | (2006.01) |
| *A01B 27/00* | (2006.01) |
| *A01C 5/06* | (2006.01) |
| *G01B 7/26* | (2006.01) |
| *G01B 11/22* | (2006.01) |
| *G01N 21/27* | (2006.01) |
| *G01N 27/22* | (2006.01) |
| *A01B 63/111* | (2006.01) |
| *G01B 21/18* | (2006.01) |

(56) References Cited

U.S. PATENT DOCUMENTS

| | | |
|---|---|---|
| 5,088,325 A | 2/1992 | Eichberger et al. |
| 5,179,347 A | 1/1993 | Hawkins |
| 5,412,219 A * | 5/1995 | Chappelle .............. G01N 21/64 |
| | | 250/253 |
| 5,430,384 A | 7/1995 | Hocker |
| 5,673,638 A | 10/1997 | Keeton |
| 6,701,857 B1 | 3/2004 | Jensen et al. |
| 7,705,616 B2 | 4/2010 | Hawkins |
| 2008/0087837 A1 | 4/2008 | Desilets et al. |
| 2010/0198529 A1 | 8/2010 | Sauder et al. |
| 2011/0247537 A1* | 10/2011 | Freed .................... A01B 35/16 |
| | | 111/140 |
| 2012/0042813 A1 | 2/2012 | Liu et al. |
| 2013/0112122 A1 | 5/2013 | Blomme et al. |
| 2014/0000919 A1 | 1/2014 | Bachman et al. |
| 2015/0020721 A1 | 1/2015 | Silbernagel et al. |
| 2015/0094917 A1 | 4/2015 | Blomme et al. |
| 2016/0037709 A1* | 2/2016 | Sauder ................... A01C 7/203 |
| | | 700/275 |

OTHER PUBLICATIONS

Exapta Solutions, Inc., "Uniform timing of emergence trumps uniform spacing for yield effect" Compiled by Matt Hagny from Paul Jasa's PowerPoint files and emails from 2007-2011, Compilation and Graphs copyright 2011, 2 pages.

Holekamp, E.R. et al., "Relation of Soil Temperature Prior to Planting to Emergence of Cottonseed", Transactions of the ASAE, 1966, pp. 203-205.

Kinze, 4900 Planter, Literature Jan. 14, 2013, 17 pages.

La Barge, Greg et al., Ohio State University Extension Fact Sheet, "Tips to Reduce Planter Performance Effects on Corn Yield", AGF-150-01, 2008.

* cited by examiner

ON-THE-GO SOIL SENSORS AND CONTROL METHODS FOR AGRICULTURAL MACHINES

CROSS REFERENCE TO RELATED APPLICATION

This is a Divisional Application of U.S. Ser. No. 14/818,435, filed Aug. 5, 2015, which claims priority to U.S. application Ser. No. 13/858,681 filed on Apr. 8, 2013, which are herein incorporated by reference in their entirety for all purposes.

FIELD OF THE INVENTION

The present invention relates generally to agricultural machines, and more specifically, to on-the-go sensors that measure soil parameters affecting optimum planting and tillage depth. An electronic control system may automatically adjust planting or tillage depth on-the-go based on measured soil parameters.

BACKGROUND OF THE INVENTION

In crops like corn, uniform seed germination and plant emergence are critical to achieve maximum yield potential. According to The Ohio State University Extension Fact Sheet *Tips to Reduce Planter Performance Effects on Corn Yield*, "Uneven emergence affects crop performance because competition from larger early-emerging plants decreases the yield from smaller later-emerging plants." "Emergence delays of 10 days or more usually translate to growth stage differences of two leaves or greater. Therefore, if two plants differ by two leaves or more, the younger, smaller plant is more likely to be barren or produce nubbins." It is generally known that no yield reduction occurs from late emergence corn as long as the plant emerges within 48 hours of nearby plants. The later a corn plant emerges beyond the 48 hour window, the greater its yield reduction. Research shows that uniform emergence can lead to an average six bushel per acre increase in corn yield.

As compared to corn, field crops such as soybeans and wheat are more effective at making up lost yields for late emerging seedlings. For instance, healthy soybean and wheat plants fill in the space of neighboring weak plants. To a certain degree, healthy soybean and wheat plants tend to produce more grain when nearby plants are behind in growth. Healthy corn plants, on the other hand, are not very effective at recapturing yield lost by nearby stunted plants. For this reason, synchronized plant emergence is critical to maximize corn yield potential and provide all plants with a fair chance at strength and vitality. As depicted in FIG. 1, late emerging seedlings 14 are slow to mature, stunted in height, and develop thinner stalks and smaller ears 18 as compared to healthy, neighboring corn plants 12 with larger ears 16 that produce higher yields. These stunted seedlings 14 steal nutrients from neighboring plants 12 and are considered by farmers to act more like weeds than productive plants. Historically in corn production, more attention has been put on achieving uniform spacing than uniform emergence; however, recent research shows that "uneven emergence has a greater adverse effect on yield than uneven spacing" according to Exapta article *Uniform timing of emergence trumps uniform spacing for yield effect*.

Synchronized plant emergence necessitates synchronized seed germination. It is known that late germinating seeds do not catch up in underground growth to earlier germinated seeds because environmental factors that affect growth between germination and emergence are generally the same for nearby plants. In other words, a seed germinated ahead of another will emerge faster because the growth rate between germination and emergence is the same for both seeds. Therefore, delayed germination means delayed plant emergence.

Plant germination depends on a few factors. A first factor is sufficient seed to soil contact. In order for the seed to absorb moisture quickly and uniformly, soil must be firmed around the seed. Seeds set in the bottom of a seed trench at planting ensure uniform seed to soil contact which leads to synchronized germination. Seed to soil contact can be maximized by proper down pressure on individual row units on a planter. A "seed firmer" can be used to improve seed to soil contact by pushing the seed firmly into the bottom of a seed trench after the planter dispenses seed into the trench. The "seed firmer" tool can improve seed germination by improving seed to soil contact in loose soil, but it can lose its effectiveness when soil voids caused by clods at the bottom of seed trench occur.

What is needed is an on-the-go means to detect soil voids in the seed trench. An on-the-go seed to soil contact sensor can be used to adjust planting depth deeper to reach solid formed soil. It could also be used to adjust a trash cleaner tool or tillage tool mounted ahead of the row to remove or pulverize clods.

A second factor for encouraging synchronized seed germination and plant emergence is adequate soil moisture. Corn seeds must imbibe an adequate amount of moisture to start and complete germination. Adequate soil moisture for corn is most simply defined as enough moisture to swell the seed triggering utilization of starch in the kernel and the emergence of a radical root. The seed must imbibe enough moisture to get root growth to the point the roots can take over supplying the young seedling with nutrients and moisture. Marginal levels of soil moisture from dry soil may cause seeds to germinate and emerge late relative to nearby seeds. Uneven soil moisture throughout the seed zone is a primary cause of uneven germination and emergence, the results of which can be yield loss. Calculating the overall soil moisture level of a field prior to planting is difficult, as soil moisture varies throughout the field and depends on several factors such as topography, weather conditions, tillage patterns, soil profile, and uneven seeding depth. Soil typically retains moisture in the valleys of a field while drying out faster on hilltops and hillsides. Empirical readings while planting have depicted up to a 2 to 1 difference in soil moisture at the same depth in different areas of the same field. Moreover, soil profiles vary in their ability to hold water. For example, FIG. 2 illustrates a field comparison of moisture levels on the top of a clayous hill 22 versus a valley 24 with loam soil. At the top of the hill 22, there is approximately 9% soil moisture at two inches in depth, while in the valley 24 there is approximately 13% soil moisture at two inches in depth. Thus, it is extremely difficult to determine the overall level of moisture in a field prior to planting.

Soil moisture levels increase as seeds are planted deeper into the soil. Thus, if the soil is dry and no precipitation is predicted in the immediate future, farmers plant seeds deeper into the soil to reach the required moisture levels to initiate germination. Soil moisture meters are known in the art as measuring moisture at different depths of the soil and can be used to help determine seed planting depths. However, commercially available sensors generally require stationary readings in order to operate. As a result, few farmers use soil moisture meters to set planting depths as they lack confidence in the soil moisture reading to achieve synchronous seed germination throughout a field.

Instead of utilizing soil moisture meters, many farmers simply determine planting depth on an ad hoc basis by digging up a planted seed. If soil surrounding the seed feels and appears to contain the required amount of moisture, planting depth is considered satisfactory. Such determinations are often made by merely pinching the soil with the fingers. Soil that sticks together is considered to maintain a satisfactory amount of moisture, while soil that fails to stick together indicates that planting depth needs to be increased. This age-old technique is largely based on past planting experience and is obviously subject to human error. In addition, the number of samples tends to be very limited in size. The bottom line is farmers do not have a good means to account for inconsistent soil moisture levels throughout a field during planting.

Thus, what is needed is a reliable, on-the-go soil moisture sensor to provide real-time readings at planting depth to the farmer while planting. On-the-go soil moisture sensors can be used to manually or automatically adjust planting depth to a depth containing optimum moisture levels for seed germination. On-the-go soil moisture sensors generally are not commercially available despite a few examples utilized in research venues. For example, V. I. Adamchuk et al. "On-the-go sensors for precision agriculture" (March 2004) discloses on-the-go soil moisture sensor research including electrical, electromagnetic, optical and radio metric sensors and methods. Lie et al. "Development of a texture/soil compaction sensor" (1996) incorporated a dielectric-based soil moisture sensor into an instrumented chisel and conducted field tests. Andrade et al. "Evaluation of a dielectric based moisture and salinity sensor for in situ applications" (2001) improved upon Lie's on-the-go sensor by overcoming the interference of temperature and salinity. Gaultney et al. "Development of a Soil Moisture Meter to Predict Corn Seed Planting Depth" (1991) and Weatherly et al. "Automatic Depth Control of a Seed Planter Based on Soil Drying Front Sensing" (1997) discloses automatically controlling planting depth based on the soil moisture readings of an on-the-go sensor. Each aforementioned reference is herein incorporated by reference in its entirety as if set forth fully herein.

On-the-go soil moisture sensors are also beneficial on non-seeder implements like field cultivators, anhydrous applicators, chisel plows, moldboard plows, vertical tillage implements, strip till and other tillage implements. Tilling soil too wet causes soil compaction which restricts root growth and can reduce yield. Soil moisture sensors can be used to adjust tilling depth to avoid soil compaction or to avoid tillage altogether until the field dries out. They could also be used with implements applying fertilizers and pesticides to adjust tillage depth to a soil moisture level that causes the fertilizer or pesticide to work more effectively for the crop. On-the-go soil moisture sensors could also be used to vary the rate of fertilizers or pesticides to make them work more effectively for the crop.

A third factor for encouraging synchronized seed germination and plant emergence is soil temperature. According to the *Tips to Reduce Planter Performance Effects on Corn Yield* article from The Ohio State University Extension, "The optimum temperature for germination and emergence is 68 degrees F. to 72 degrees F. Emergence occurs in five to six days at these temperatures. Soil temperatures below 50 degrees F. dramatically slow germination and emergence. Individual seeds in a furrow may be subject to different temperature and moisture conditions due to placement."

Soil temperature decreases the deeper seed is planted. An on-the-go soil temperature sensor can be used on planting implements to adjust planting depth to an optimum temperature level for seed germination. It can also be used with non-seeder implements to adjust tillage depth for the purpose of making fertilizers and pesticides more effective for the crop. It can also be used to vary the rate of fertilizers and pesticides to make them more effective for the crop.

A fourth factor for encouraging synchronized seed germination and plant emergence is proper planting depth. It's already been shown optimum planting depth is dependent on the aforementioned factors; however, sensing the actual planting depth from the top of the soil to the bottom of the seed trench is important on its own accord. For example, plant residue can cause the depth regulation member (e.g. gauge wheels) of a planter row unit to ride up on top of the residue causing a shallower cut seed trench than intended. Gauge wheel load sensors are known in the art to sense when the row unit is cutting a seed trench at the intended depth; however, they don't account for the depth error from plant residue and they can't measure the magnitude of the depth of cut of the seed trench. On-the-go seed trench depth sensors provide feedback for adjusting planting depth to maintain a desired target seed trench depth. They can also provide cutting depth information to non-seeder tillage implements for the purpose of tilling at an intended depth.

BRIEF SUMMARY OF THE INVENTION

Therefore it is a primary object, feature, or advantage of the present invention to improve upon the state of the art.

It is a further object, feature, or advantage of the present invention to improve yield by encouraging uniform seed germination and plant emergence.

It is a further object, feature, or advantage of the present invention to provide a control system for sensing soil moisture on-the-go while planting and adjust planting depth, accordingly.

A still further object, feature, or advantage of the present invention is providing a method to automatically adjust seed planting depth on-the-go in relation to soil moisture.

Yet another object, feature, or advantage of the present invention is to provide a control system for sensing seed to soil contact on-the-go while planting and adjust planting depth, accordingly.

Another object, feature, or advantage of the present invention is providing a method to automatically adjust planting depth on-the-go in relation to seed to soil contact.

An additional object, feature, or advantage of the present invention is to provide a planter for sensing soil moisture and seed to soil contact on-the-go and adjust planting depth and row unit down pressure, accordingly.

Yet another object, feature, or advantage is to provide a commercially viable, easy to use, reliable, on-the-go soil moisture and seed to soil contact sensor.

One or more of these and/or other objects, features, or advantages of the present invention will become apparent from the Specification and claims that follow. No single embodiment need meet all of these objects, features, or advantages and different embodiments may meet different objects, features, or advantages. The present invention is not to be limited by or to these objects, features, or advantages.

According to one aspect of the present invention, a method of adjusting seed planting depth on-the-go for a row unit of a planter is provided. The method includes providing a control system operatively connected to the planter, the control system comprising a soil moisture sensor, an actuator for adjusting a seed planting depth, and an intelligent control electrically connected to the actuator, and the soil moisture sensor. The method further includes measuring moisture at the planting depth with the soil moisture sensor as seeds are planted to provide soil moisture data. The method further includes analyzing sensor data to provide seed planting depth adjustments, the sensor data including the soil moisture data. The method further includes adjusting seed planting depth on-the-go using the actuator based on the seed planting depth adjustments. The control system may further include a soil contact sensor electrically connected to the intelligent control and the method may further include measuring soil contact with the soil contact sensor as the seeds are planted to provide soil contact data and wherein the sensor data further comprises the soil contact data. The control system may further include a depth sensor electrically connected to the intelligent control and the method may further include measuring depth with the depth sensor as the seeds are planted to provide depth data and wherein the sensor data further comprises the soil contact data.

According to another aspect of the present invention, a system for providing on-the-go monitoring for use in automatically adjusting seed planting depth on-the-go in a planter having at least one row unit is provided. The system may include a seed firmer associated with a row unit of the planter, a first sensor operatively connected to the seed firmer to provide sensor data, an intelligent control electrically connected to the first sensor and adapted to receive the sensor data, and an actuator associated with the row unit of the planter. The intelligent control is configured to monitor sensor data from the first sensor operatively connected to the seed firmer and automatically adjust the seed planting depth on-the-go for the first row unit of the planter using the actuator associated with the row unit of the planter. The system may further include a monitor operatively connected to the intelligent control and wherein the monitor is configured to display information based on the sensor data. The first sensor may be a seed trench depth sensor, a soil temperature sensor, a soil moisture sensor or a soil contact sensor. Where a second sensor is used, the first sensor may be a seed trench depth sensor, a soil temperature sure, a soil moisture sensor, or a soil contact sensor and the second sensor may be a different type of sensor.

According to another aspect of the present invention, a system includes a planter for planting seeds, the planter having at least one row unit. The system further includes a soil moisture sensor attached to the row unit, a monitor for displaying soil moisture readings, an actuator for adjusting seed planting depth, and an intelligent control operatively connected to the monitor, actuator, and soil moisture sensor. The soil moisture sensor is configured to measure moisture readings at the planting depth as seeds are planted on-the-go. The intelligent control receives the moisture readings from the soil moisture sensors and displays the moisture readings on the monitor. The control system automatically adjusts seed planting depth on-the-go through the actuator in relation to the level of moisture in the soil.

According to another aspect, a system for providing on-the-go monitoring for use in automatically adjusting seed planting depth on-the-go in a planter having at least one row unit is provided. The system includes a seed firmer associated with a row unit of the planter, a first sensor operatively connected to the seed firmer to provide sensor data, an intelligent control electrically connected to the first sensor and adapted to receive the sensor data, an actuator associated with the first sensor, and wherein the intelligent control is configured to monitor sensor data from the first sensor operatively connected to the seed firmer and automatically adjust the seed planting depth on-the-go for the first row unit of the planter using the actuator associated with the first sensor. The first sensor and the actuator may be positioned at the same row unit. Alternatively, the first sensor and the actuator may be positioned at the same or different row units within a section of the planter having multiple row units.

According to another aspect, a system is provided. The system includes a planter for planting seeds, the planter having at least one row unit, a soil moisture sensor attached to the planter, a monitor for displaying soil moisture readings, an actuator for adjusting seed planting depth, and an intelligent control operatively connected to the monitor, actuator, and soil moisture sensor. The soil moisture sensor is configured to measure moisture readings at the planting depth as seeds are planted on-the-go. The intelligent control receives the moisture readings from the soil moisture sensors and displays the moisture readings on the monitor. The control system automatically adjusts seed planting depth on-the-go through the actuator in relation to level of moisture in the soil.

According to another aspect of the present invention a system for adjusting seed planting depth on-the-go based on feedback from an on-the-go soil moisture sensor on a planter, is provided. A desired target soil moisture is inputted by the user into a monitor located in a tractor attached to the planter. The monitor is operatively connected to the control system which includes an intelligent control operatively connected to soil moisture sensors located on individual row units of the planter. The soil moisture sensors measure moisture at the planting depth, as seeds are planted on-the-go. Real-time moisture readings taken from the soil moisture sensors are relayed to the intelligent control and further displayed to the user on the monitor. The control system compares the real-time soil moisture readings with the target soil moisture, and adjusts seed planting depth on-the-go to reach the target soil moisture required for optimum seed emergence. Seed planting depth can be automatically adjusted through various types of actuators located on each individual row unit and operatively connected to the intelligent control. Thus, the control system adjusts seed planting depth on-the-go to assist in maximizing yield potential based on feedback from soil moisture sensors located on the row units.

According to another aspect of the present invention a planter for planting seeds is provided for adjusting seed planting depth and seed to soil contact on-the-go based on feedback from an on-the-go soil moisture sensor and seed to soil contact sensor on the planter. A desired target soil moisture and seed to soil contact is inputted by the user into a monitor located in a tractor attached to the planter. The monitor is operatively connected to a control system comprised of an intelligent control operatively connected to soil moisture sensors and seed to soil contact sensors located on individual row units of the planter. The sensors measure soil moisture and seed to soil contact at the planting depth, as seeds are planted on-the-go. Real-time moisture readings and seed to soil contact readings taken from the sensors are relayed to the intelligent control and further displayed to the user on the monitor. The control system compares the real-time soil moisture and seed to soil contact readings with the target soil moisture and seed to soil contact, and adjusts seed planting depth and row unit down pressure on-the-go to reach the desired target soil moisture and seed to soil contact needed for optimum seed emergence. Seed planting depth and row unit down pressure can be automatically adjusted through various types of actuators located on each individual row unit and operatively connected to the intelligent control. Thus, the planter adjusts seed planting depth and row unit down pressure on-the-go to assist in maximizing yield potential based on feedback from soil moisture and seed to soil contact sensors located on the row units.

According to another aspect, a method of adjusting seed planting depth on-the-go is provided. The method includes providing a system comprising (a) a planter for planting seeds, the planter including at least one row unit, (b) a soil moisture sensor attached to the planter, (c) a monitor for displaying soil moisture readings, (d) an actuator for adjusting seed planting depth, and (f) an intelligent control operatively connected to the monitor, actuator, and the soil moisture sensor. The method further includes measuring moisture at the planting depth with the soil moisture sensor as seeds are planted to provide soil moisture data, analyzing sensor data to provide seed planting depth adjustments, the sensor data including the soil moisture data, and adjusting seed planting depth on-the-go using the actuator based on the seed planting depth adjustments.

According to another aspect, a method of monitoring and displaying readings associated with a soil moisture sensor on an agricultural machine as the agricultural machine traverses a field is provided. The method includes sensing soil moisture data with the soil moisture sensor on the agricultural machine as the agricultural machine traverses the field and displaying on a display associated with the agricultural machine a representation of soil moisture. The representation of the soil moisture may include soil moisture as percent content of soil. The representation of the soil moisture may be a soil moisture range in which the soil moisture falls. The agricultural machine may include a seed firmer with the soil moisture sensor mounted on the seed firmer. The soil moisture sensor may be mounted on the agricultural machine to measure moisture at or proximate a bottom of a seed trench formed using the agricultural machine. The agricultural machine may be an agricultural tillage machine and the soil moisture sensor may be mounted on the agricultural machine to measure moisture at a cutting depth of the agricultural tillage machine. The method may further include automatically controlling tillage depth of the agricultural tillage machine using the soil moisture data. The method may further include automatically controlling application rate of at least one agricultural input based on the soil moisture data, the at least one agricultural input selected from the set consisting of pesticides, fertilizers, growth regulators, defoliants, and seeds.

According to another aspect, a method of monitoring and displaying readings associated with a soil temperature sensor on an agricultural machine as the agricultural machine traverses a field is provided. The method may include sensing soil temperature data with the soil temperature sensor on the agricultural machine as the agricultural machine traverses the field and displaying on a display associated with the agricultural machine a representation of soil temperature. The representation of the soil temperature may be in degrees Fahrenheit or degrees Celsius. The representation of soil temperature may be a range indicator format. The soil temperature sensor may be mounted on a seed firmer of the agricultural machine such as in a position suitable to measure temperature at or proximate a bottom of a seed trench formed using the agricultural machine. The agricultural machine may be an agricultural tillage machine and the soil temperature sensor may be mounted on the agricultural machine to measure temperature at a cutting depth of the agricultural tillage machine. The method may further include automatically controlling application rate of at least one agricultural input based on the soil temperature data, the at least one agricultural input selected from the set consisting of pesticides, fertilizers, growth regulators, defoliants, and seeds.

According to another aspect, a method of monitoring and displaying readings associated with a sensor measuring seed to soil contact on a seeder as the seeder seeds a field is provided. The method may include sensing seed to soil contact data with the sensor on the seeder as the seeder seeds the field and displaying on a display associated with the agricultural machine a representation of seed to soil contact. The representation of seed to soil contact may be in a range indicator format. The range indicator format may use color coding to specify different ranges. The sensor may be mounted on a seed firmer of the seeder. The sensor may be mounted on the seeder to measure seed to soil contact at or proximate a bottom of a seed trench.

According to another aspect, a method of monitoring and displaying readings associated with a sensor measuring cutting depth of a seed trench on a seeder as the seeder seeds a field is provided. The method includes sensing cutting depth with the sensor on the seeder as the seeder seeds the field and displaying on a display associated with the seeder a representation of cutting depth of the seed trench. The representation of the cutting depth provides a linear distance dimension. The representation of the cutting depth may include a range indicator format. The sensor may be mounted on a seed firmer of the seeder. The sensing cutting depth with the sensor may provide for distinguishing between plant residue on top of ground and soil and wherein the plant residue on the top of the ground is not included in the cutting depth.

According to another aspect, an apparatus is provided. The apparatus includes a seed firmer and a seed count sensor integrated into the seed firmer. The apparatus may further include an intelligent control electrically connected to the seed count sensor and a display operatively connected to the intelligent control.

Different aspects may meet different objects of the invention. Other objectives and advantages of this invention will be more apparent in the following detailed description taken in conjunction with the figures.

DESCRIPTION OF FIGURES

The above mentioned features of this invention, and the methods of attaining them, will become more apparent and the invention itself will be better understood by reference to the following description of embodiments of the invention taken in conjunction with the accompanying figures, wherein:

FIG. 13 is a diagram of another example of a seed-firm with one or more sensors built-in.

DETAILED DESCRIPTION OF THE INVENTION

The present invention includes systems and methods for use in adjusting seed planting depth and row unit down pressure to account for varying levels of soil moisture in a field when planting to minimize occurrences of late emerging corn seedlings.

Figure 1:
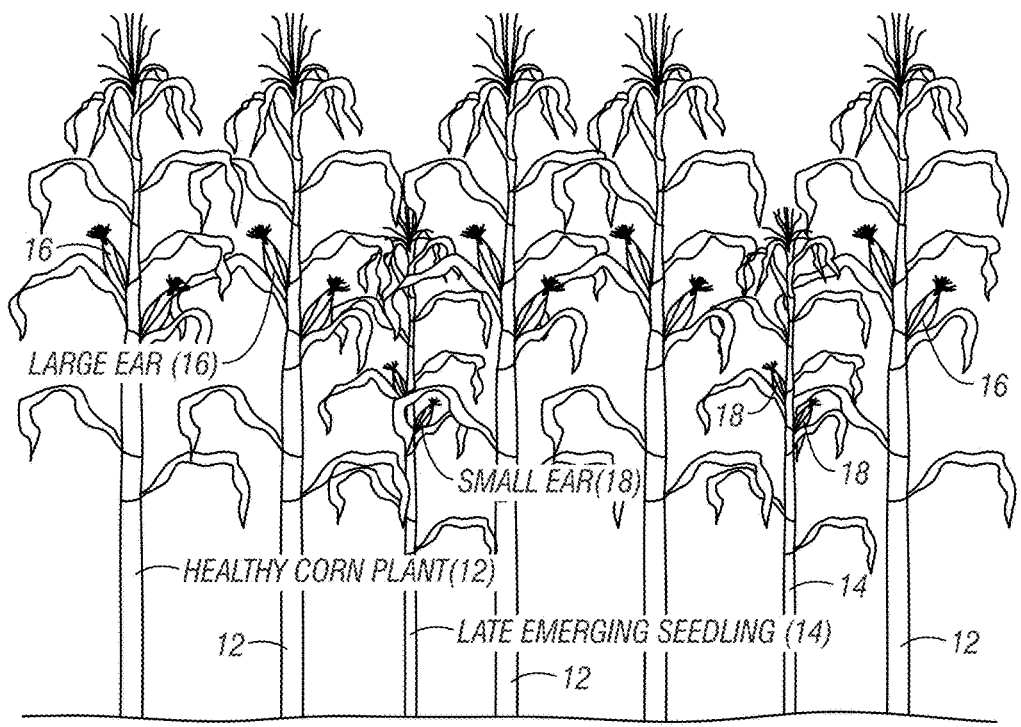
FIG. 1 is a depiction of a healthy corn plant as compared to a late emerging corn plant.
Figure 2:
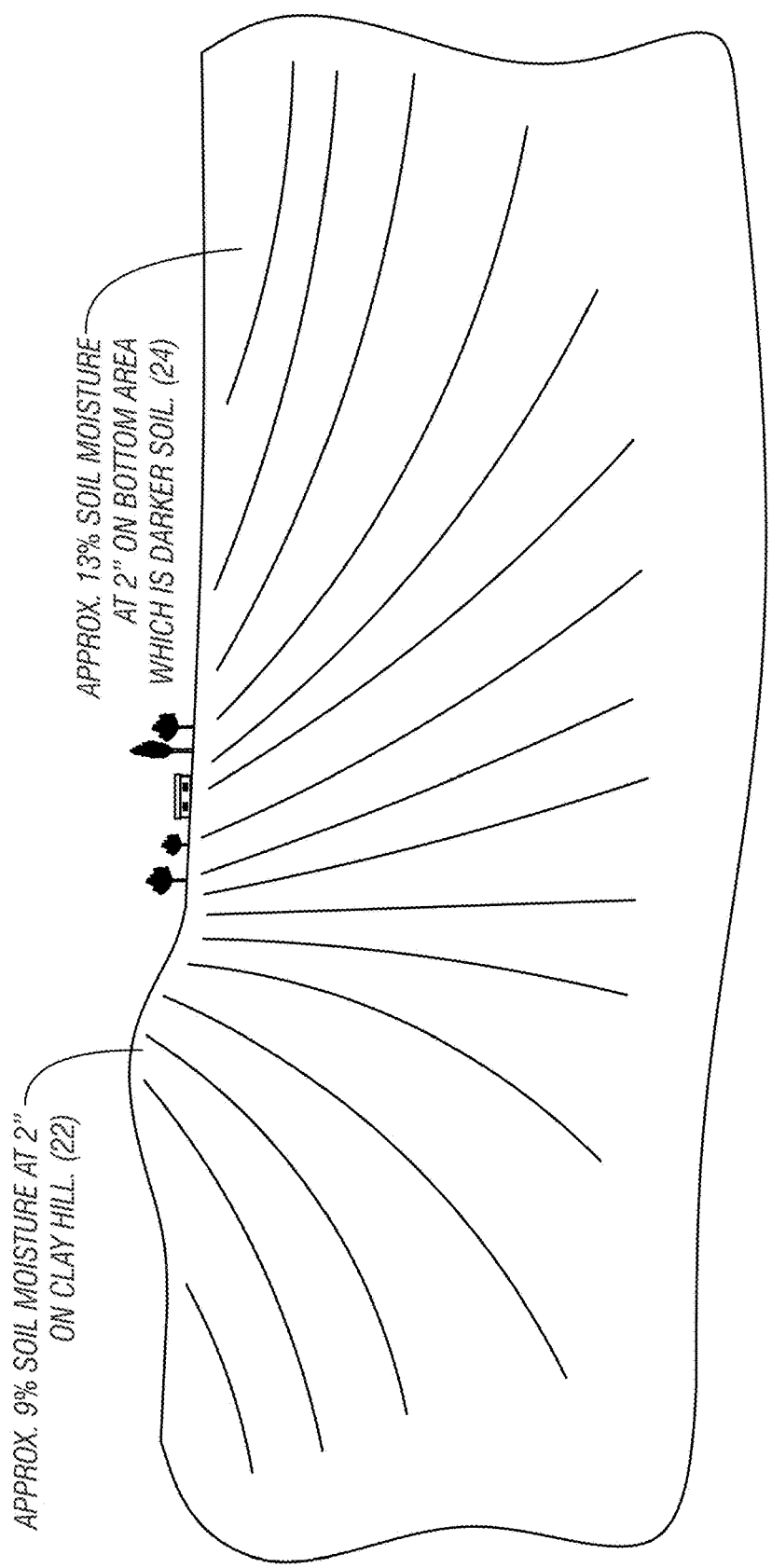
FIG. 2 is a depiction of soil moisture variation in a crop field.
Figure 3:
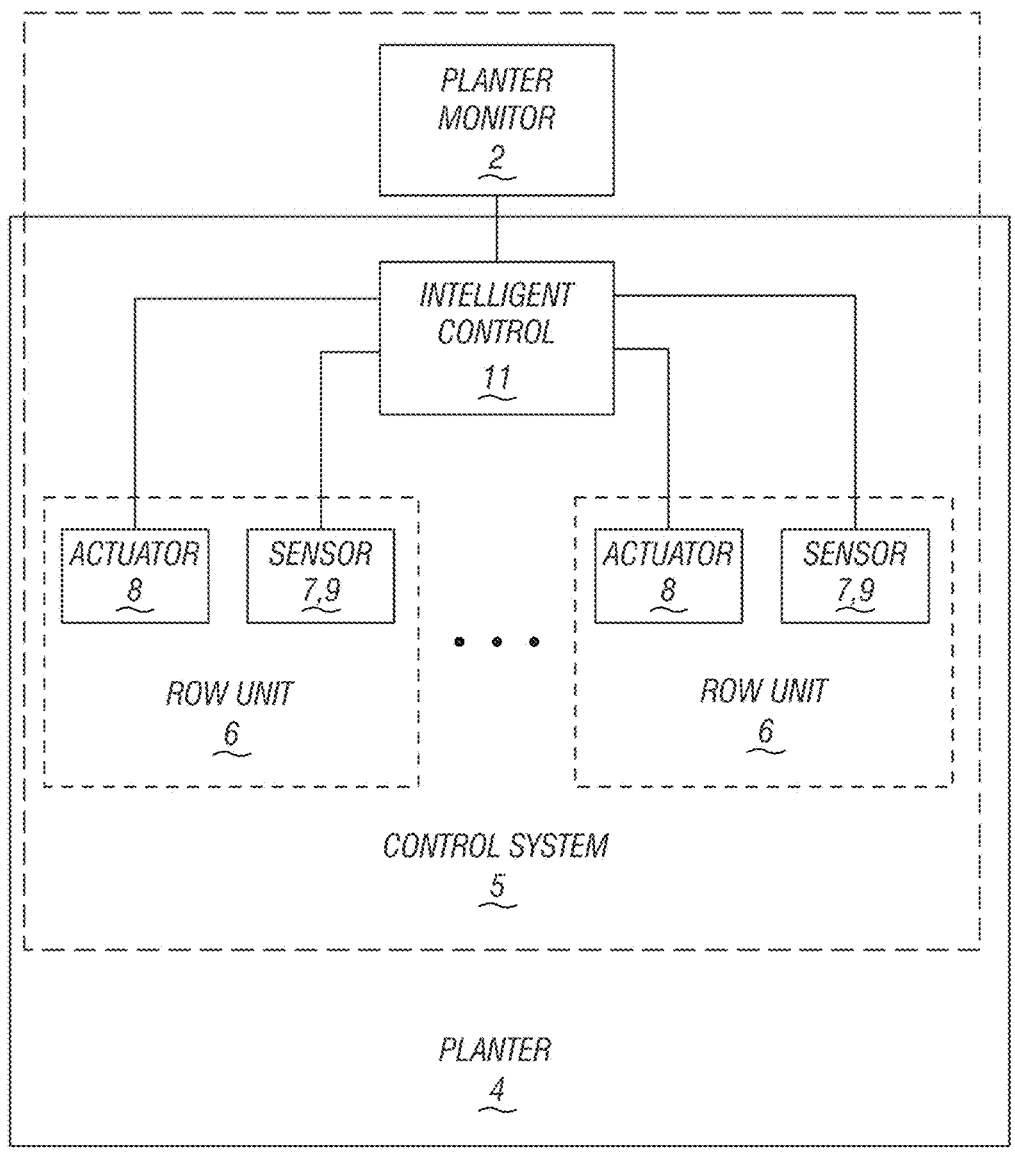
FIG. 3 illustrates one embodiment of a system of the present invention.

FIG. 3 illustrates one example of a system which includes a planter 4 having a control system 5. The control system 5 may include an intelligent control 11 operatively connected to a monitor 2. There may be a plurality of row units 6. For each row unit 6, there is an actuator 8 and sensors 7, 9. The sensors 7, 9 may include a soil moisture sensor, a seed to soil contact sensor, soil temperature sensor and seed trench depth sensor for adjusting seed planting depth and row unit down pressure on-the-go while planting.

Figure 4:
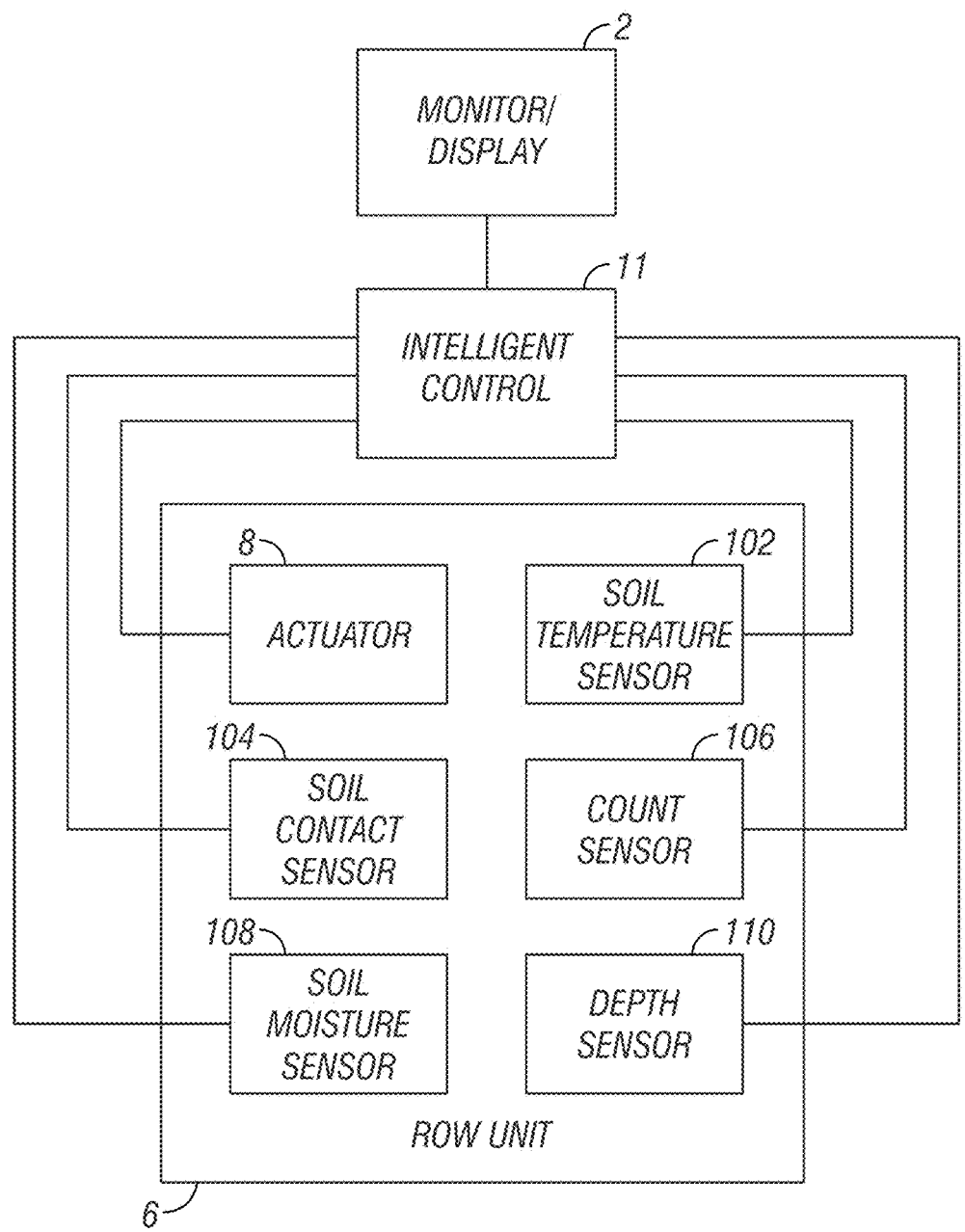
FIG. 4 illustrates another embodiment of a system of the present invention for adjusting planting depth and/or row unit down pressure on-the-go based on feedback from an on-the-go soil moisture sensors and/or seed to soil contact sensors on a planter.

FIG. 4 illustrates another example of the invention. As shown in FIG. 4, an intelligent control 11 is operatively connected to a monitor or display 2. The intelligent control unit 11 is also operatively connected to an actuator 8 and to one or more of various examples of sensors on the row unit. Examples of such sensors include a soil temperature sensor 102, a soil contact sensor 104, a count sensor 106, a soil moisture sensor 108, and a depth sensor 110. The soil moisture sensor 108 may be a dielectric or capacitance sensor, or an optical sensor for detecting moisture when put in contact of a soil. The soil moisture sensor may placed at the bottom or one of the sides of a seed trench in which seeds are deposited. It is contemplated that more than one soil moisture sensor may be used. The count sensor 106 may be used detect or count the number of seeds planted in a seed furrow. Dielectric or optical sensors may be used to do so. The soil contact sensor 104 may be used to sense seed to soil contact. Dielectric or optical sensors or contact sensors may be used to do so. The soil temperature sensor 102 may be a thermocouple sensor or other sensor used to detect temperature. The depth sensor 110 may be used to measure seed furrow depth and may include dielectric or optical sensors to detect the depth of the furrow by measuring height of a seed furrow sidewall.

Figure 7:
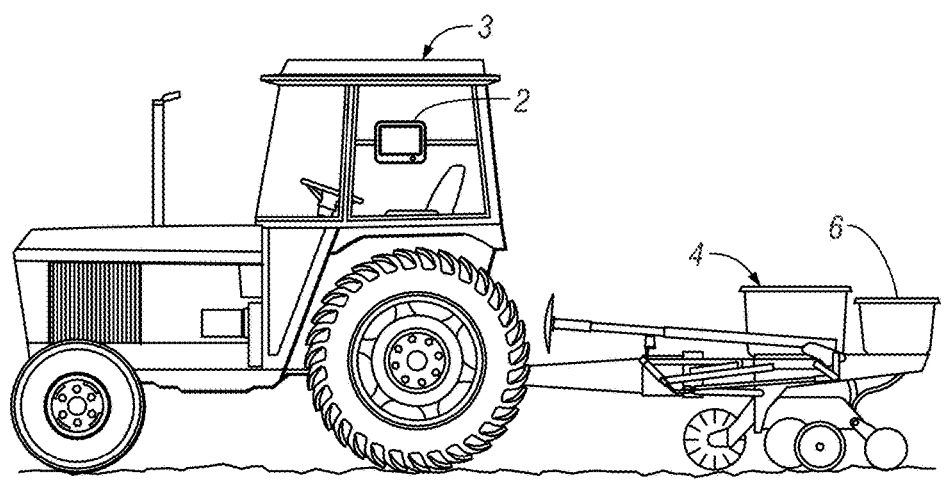
FIG. 7 is a diagram of an embodiment of the present invention attached to a tractor.

The monitor 2 may be used to display soil moisture readings, such a monitor may also be used for a number of other purposes associated with planting such as informing the user whether he/she is within a target planting population, finding and displaying hidden mechanical problems, adjusting vacuum pressure, displaying transmissions, speed, row unit weight, field acres planted, GPS, seed singulation, plot maps, and alerting the user to skipped and clogged rows, as well as other information which is measured or derived directly or indirectly from parameters which are measured. As illustrated in FIG. 7, the monitor 2 is typically located in the cab of a tractor 3 attached to the planter 4.

Returning to FIG. 4, the intelligent control 11 may be a processor or a microcontroller, integrated circuit or other type of intelligent control programmed or otherwise configured to control the system. The actuator 8 may be a hydraulic or pneumatic actuator or other type of actuator for adjusting seed planting depth. There may be multiple row units 6 on the planter 4, and one or more soil moisture sensors 7 attached to each row unit 6. Each soil moisture sensor 7 may be configured to measure moisture at the planting depth as seeds are planted on-the-go. Real-time moisture readings taken from the soil moisture sensors 7 may be relayed to the intelligent control 11 and displayed on the monitor 2 for review by the user. The control system may provide for comparing the real-time soil moisture readings with a target soil moisture previously determined by the user to reach optimum seed emergence. In light of this comparison, the control system may then adjust seed planting depth on-the-go through the actuator 8 in relation to the level of moisture in the soil to assist in increasing yield potential. It is recognized that this adjustment may be automatically performed by the intelligent control 11 operatively connected to the actuator 8. It is further recognized that various types of soil moisture sensors 7 may be utilized, such as dielectric or optical sensors.

Figure 5:
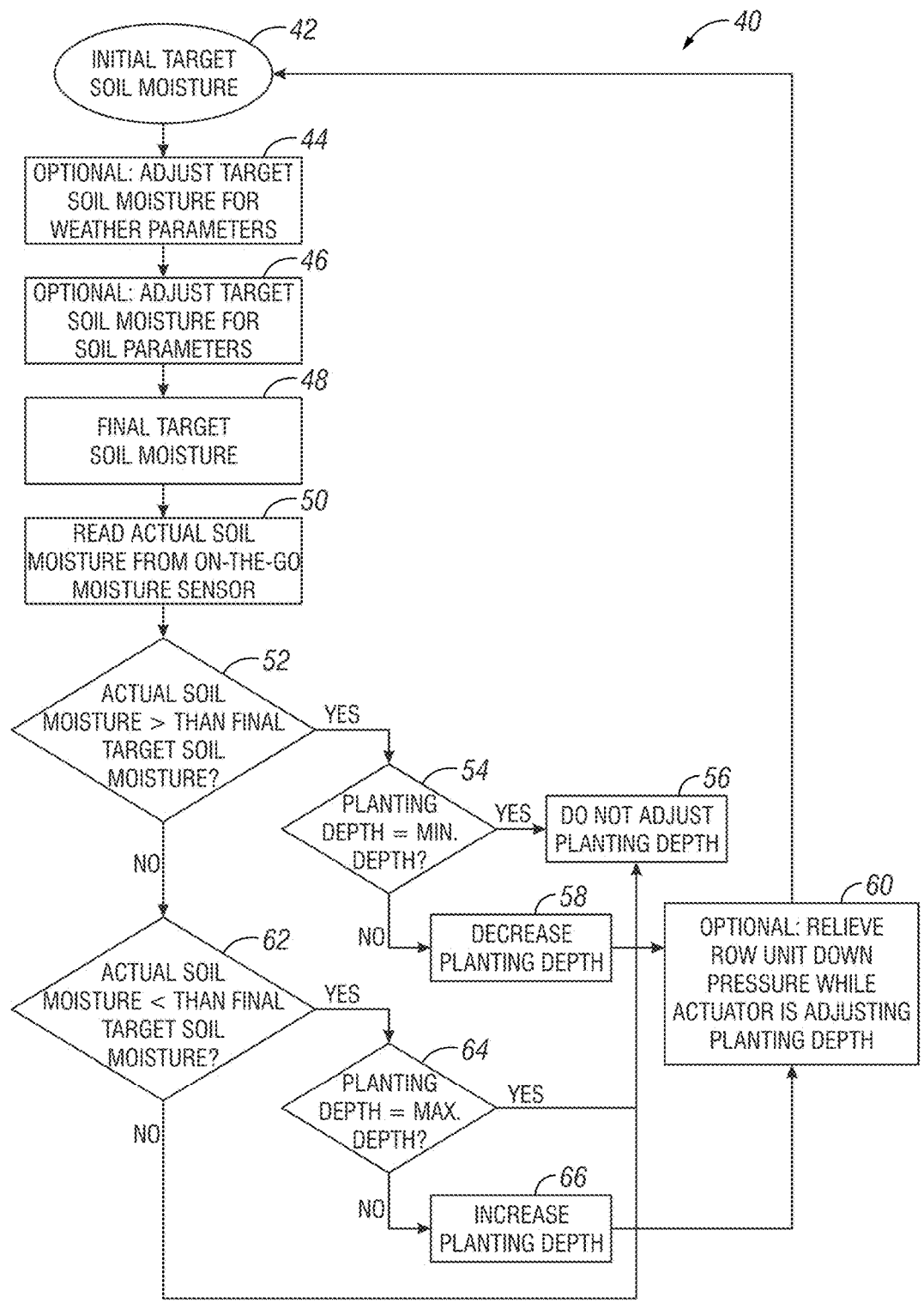
FIG. 5 is a method of adjusting seed planting depth to ensure satisfactory soil moisture for optimum seed emergence.

FIG. 5 illustrates one example of a method 40 of the present invention. The method may be used for adjusting planting depth on-the-go based on feedback from an on-the-go soil moisture sensor and may be implemented as a control algorithm using the intelligent control. The soil moisture sensor measures moisture at the planting depth, as seeds are planted and this information is used to control planting depth. Initially, in step 42, a user may have previously identified the target soil moisture required in a field for optimum seed emergence and input it into the system. The initial target soil moisture may be adjusted for weather parameters such as future precipitation forecasts in step 44. The initial target soil moisture may also be adjusted for soil profiles and field topography in step 46. In light of such factors, the desired final target soil moisture may be determined in step 48. In step 48, the final target soil moisture may be determined. Alternatively, this final target soil moisture may also be input by the user into a monitor. In step 50, moisture is measured at the planting depth as seeds are planted on-the-go by the soil moisture sensors. In step 52, a determination is made as to whether the actual soil moisture is greater than the final target soil moisture. If it is, then in step 54 a determination is made as to whether the planting depth is equal to the minimum planting depth. If the planting depth is equal to the minimum depth then in step 56 a determination is made to not adjust the planting depth. If the planting depth is not equal to the minimum planting depth as determined in step 54, then in step 58 the planting depth is decreased.

Returning to step 52, if the actual soil moisture is not greater than the final target soil moisture then in step 62 a determination is made as to whether the actual soil moisture is less than the final target soil moisture. If it is then in step 64 a determination is made as to whether the planting depth is equal to the maximum planting depth. If it is then in step 56 the planting depth is not adjusted. If it is not, then in step 66 the planting depth is increased. Returning to step 62, if the actual soil moisture is not greater than the final target soil moisture then in step 56 the planting depth is not adjusted.

After changing the planting depth, whether it be decreasing planting depth in step 58 or increasing planting depth in step 66, the process may perform the optional step of relieving the row unit down pressure while the actuator is adjusting planting depth. Regardless of whether or not the optional step is performed, the process returns to step 42.

Figure 6:
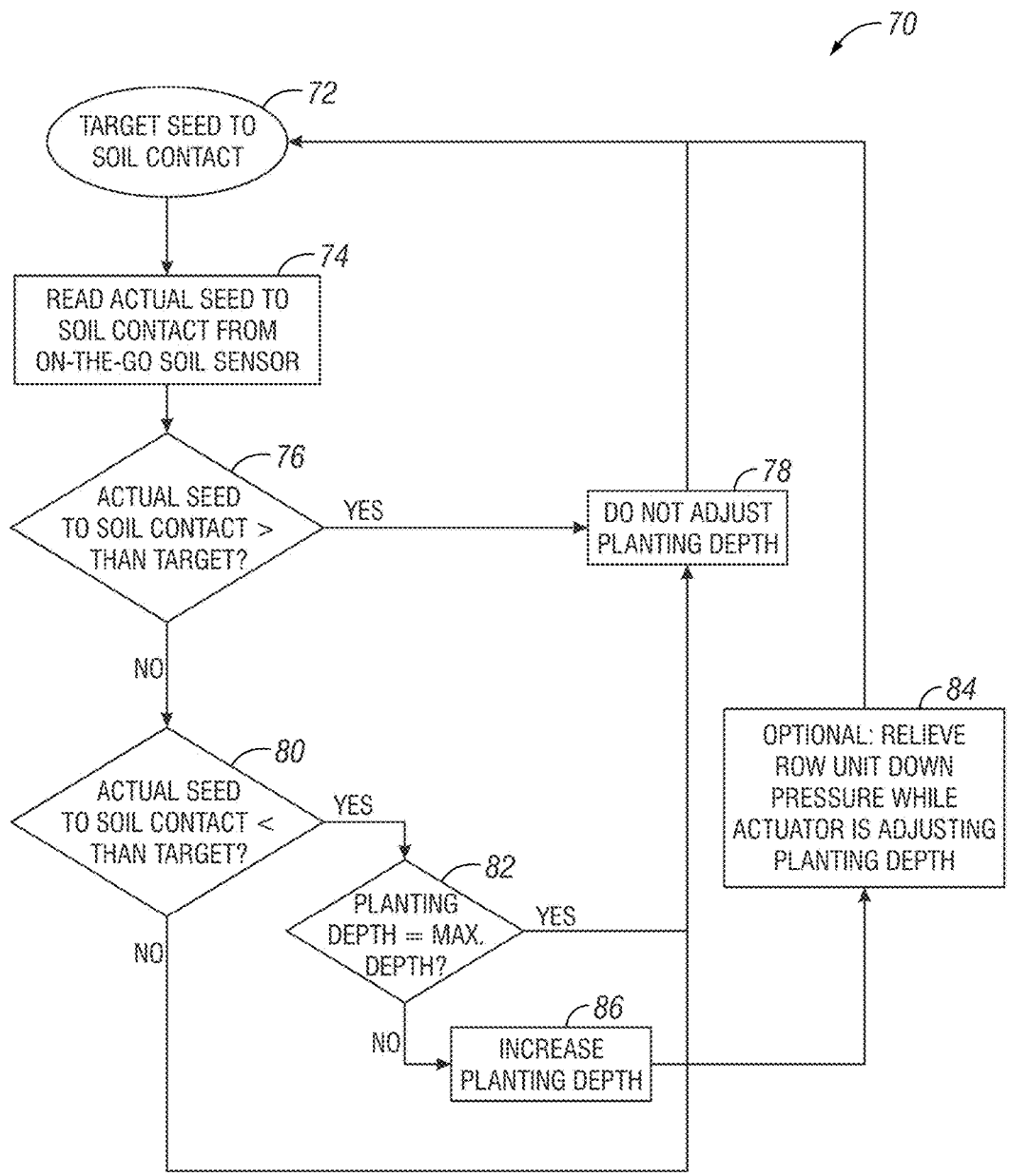
FIG. 6 is a method of adjusting row unit down pressure to ensure satisfactory seed to soil contact for optimum seed emergence.

FIG. 6 illustrates another example of a method 70 of the present invention. The method may be performed by an intelligent control as a control algorithm for adjusting planting depth on-the-go based on feedback from an on-the-go seed to soil contact sensor. The seed to soil contact sensor measures at the planting depth, as seeds are planted and provides for adjusting planting depth based on measurements from the soil contact sensor. Initially, a user may identify a desired target seed to soil contact required for optimum seed emergence such as by inputting the target seed to soil contact into a monitor device. The target seed to soil contact is provided in step 72. In step 74, the actual seed to soil contact is sensed or measured from an on-the-go soil sensor. In step 76, a determination is made as to whether the actual seed to soil contact is greater than the target. If it is then in step 78 the planting depth is not adjusted. If it is, then in step 80, a determination is made as to whether the actual seed to soil contact is less than the target. If it is not, then in step 78 the planting depth is not adjusted. If it is, then in step 82 a determination is made as to whether the planting depth is at the maximum depth. If it is then in step 78 the planting depth is not adjusted. If it is not, then in step 84 the planting depth is increased. Then an optional step 84 may be performed which involves relieving the row unit down pressure while the actuator is adjusting planting depth. Regardless of whether the planting depth is adjusted or not, the process then returns to step 72 to be repeated.

FIG. 7 which has been previously referenced includes a tractor 3 with a cab in which the monitor 2 may be placed. The tractor 4 pulls the planter 4 which includes row units 6.

Figure 8:
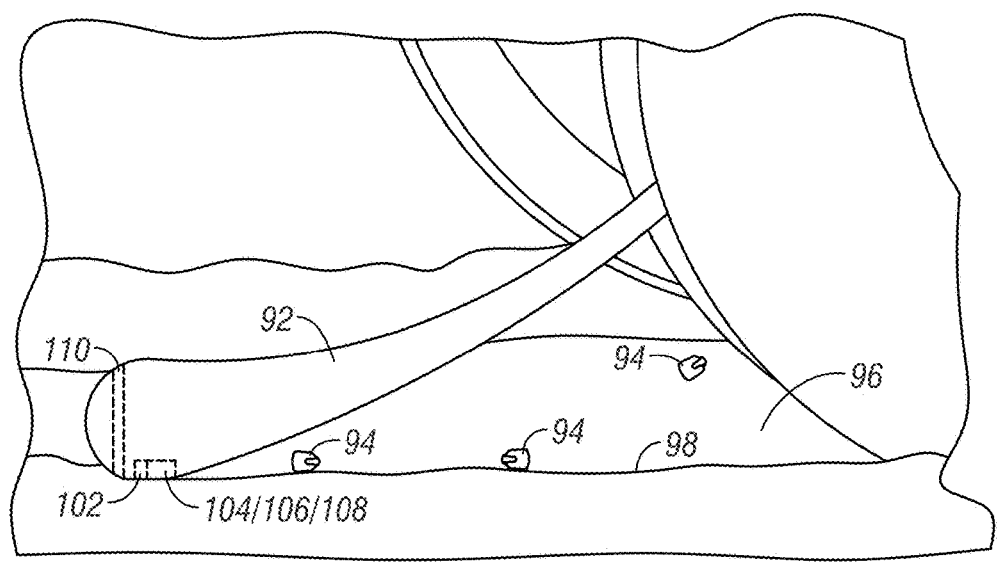
FIG. 8 is a depiction of soil moisture sensors or seed to soil contact sensors built into the bottom and/or sides of a seed firmer.

FIG. 8 illustrates a seed firmer 92 which may be present on each row unit of a planter in order to improve seed to soil contact. Seed to soil contact sensors and/or soil moisture sensors or other sensors may be incorporated into the base, sides, or base and sides of the seed firmer 92. As shown in FIG. 8, a soil contact sensor 104 is shown, as is a soil temperature sensor 102, a seed count sensor 106, a soil moisture sensor 108, and a depth sensor 110. The seed firmer 92 improves seed to soil contact by pushing the seed 94 firmly into the bottom 98 of a seed trench 96 created by a planter when planting. Thus, the seed firmer tool 92 operatives conventionally with respect to improving seed germination but also uses sensors readings from the included sensors to prevent seed 94 from being planted in soil too dry for germination, seed planted too deep or too shallow or other conditions.

Figure 9:
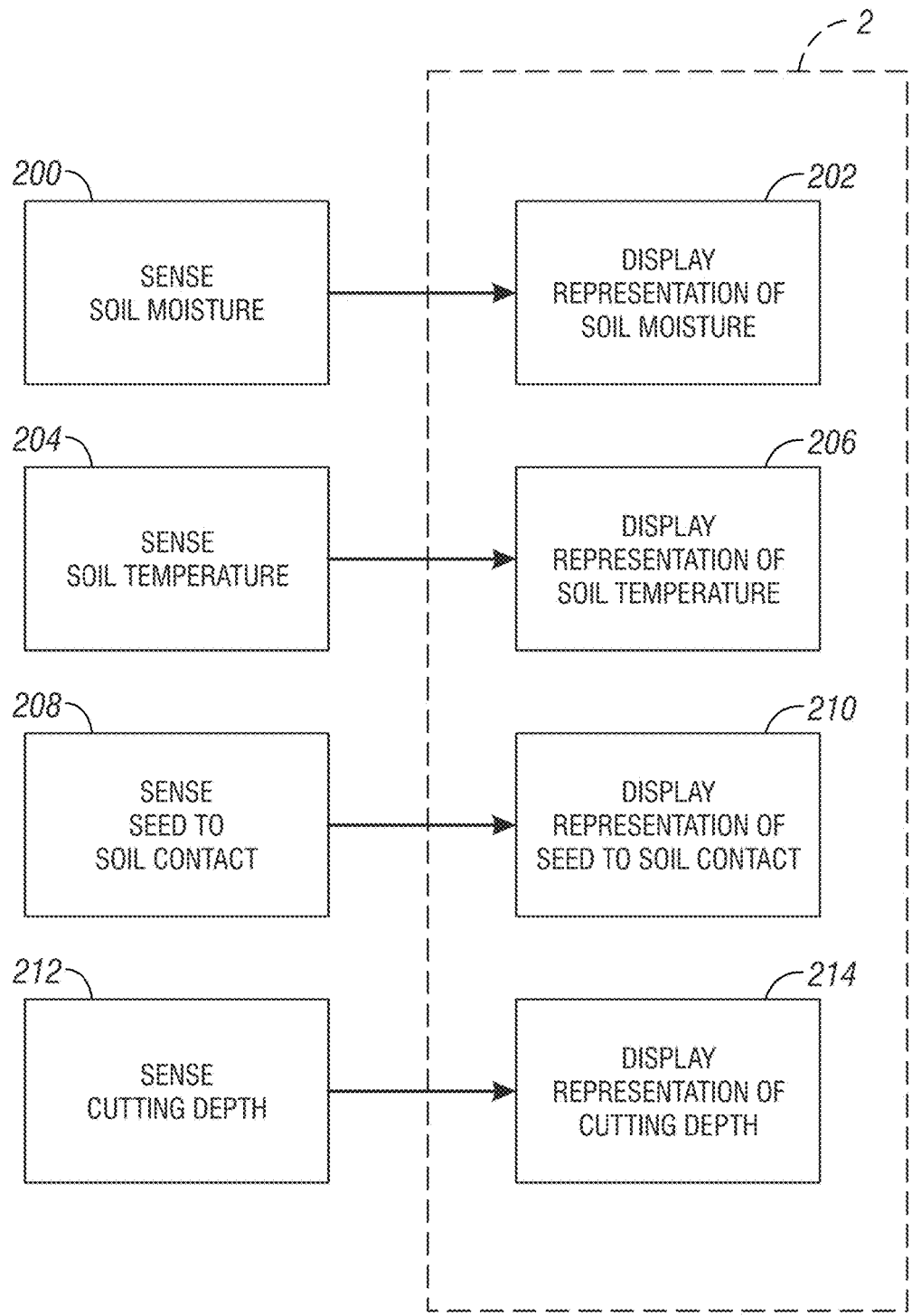
FIG. 9 is a diagram illustrating various methods of sensing data and displaying representations of the data.

FIG. 9 is a diagram illustrating various methods of sensing data and displaying representations of the data. As shown in FIG. 9, a step 200 of sensing soil moisture may be performed and a step 202 of displaying a representation of the soil moisture on a display 2 may be performed. Similarly, a step 204 of sensing soil temperature may be performed and a step 206 of displaying a representation of soil temperature on the display 2 may be performed. Similarly, a step 208 of sensing seed-to-soil contact may be performed and a step 210 of displaying a representation of seed-to-soil contact on display 2 may be performed. Similarly, a step 212 of sensing cutting depth may be performed and a step 214 of displaying a representation of cutting depth on display 2 may be performed. For any sensed information the present invention contemplates that associated information may be displayed in various types of quantitative or qualitative representations which may indicate specific values, a range of values, or an interpretation of a value.

Figure 10:
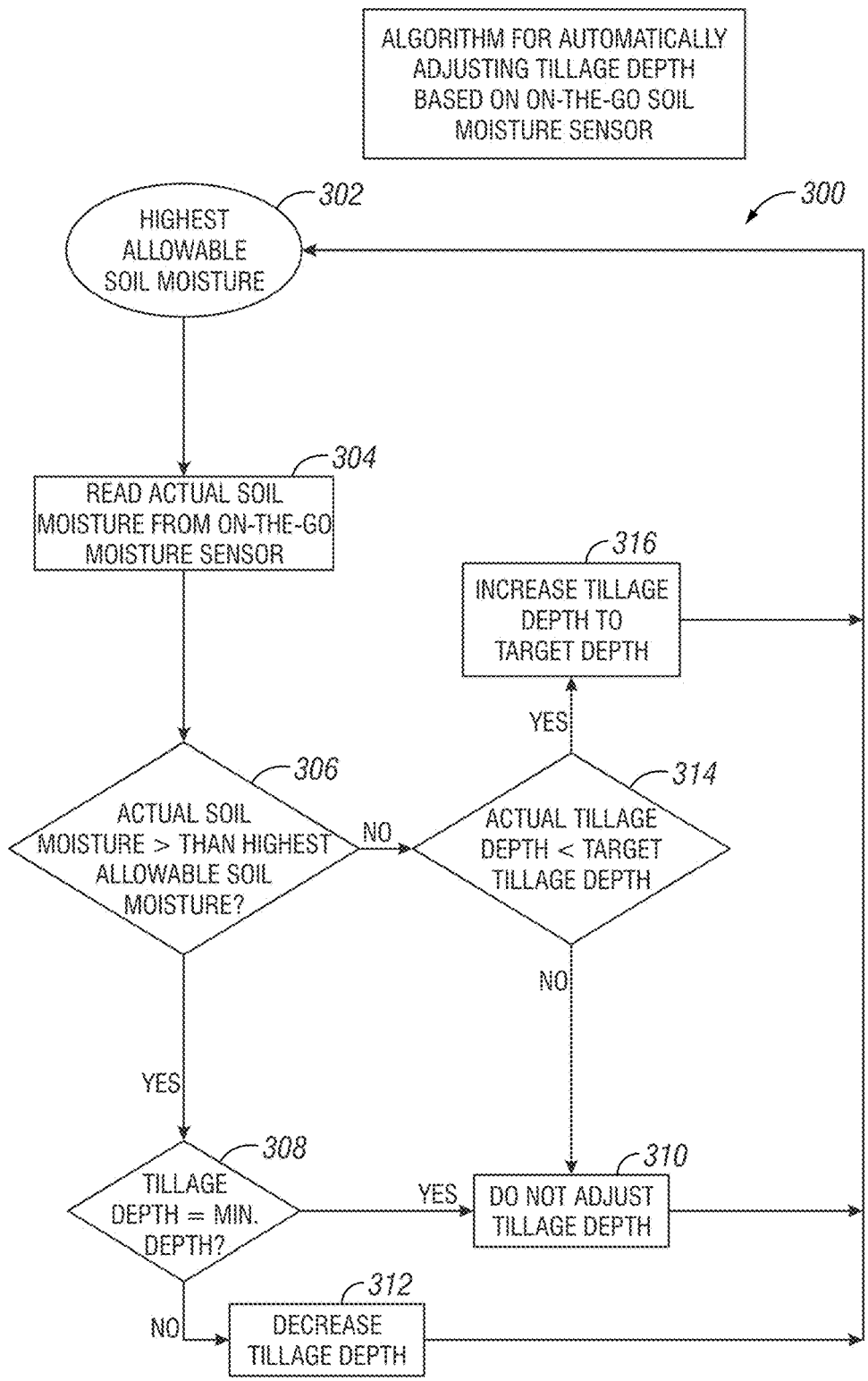
FIG. 10 is a method for automatically adjusting tillage depth based on an on-the-go moisture sensor.

FIG. 10 is a method 300 for automatically adjusting tillage depth based on an on-the-go moisture sensor. As shown, there is a highest allowable soil moisture 302. In step 304 an actual soil moisture is read from the on-the-go soil moisture. In step 306, a determination is made as to whether or not the actual soil moisture is greater than the highest allowable soil moisture. If it is, then in step 308 a determination is made as to whether the tillage depth is equal to the minimum tillage depth. If it is, then in step 310, the tillage depth is not adjusted. If it is not, then in step 312, the tillage depth is decreased. Returning to step 306 if the actual soil moisture is not greater than the highest allowable soil moisture then in step 314, a determination is made as to whether the actual tillage depth is less than the target tillage depth. If it is, then in step 316, the tillage depth is increased to the target depth. Thus, tillage depth may be automatically adjusted based on the on-the-go soil moisture sensor.

Figure 11:
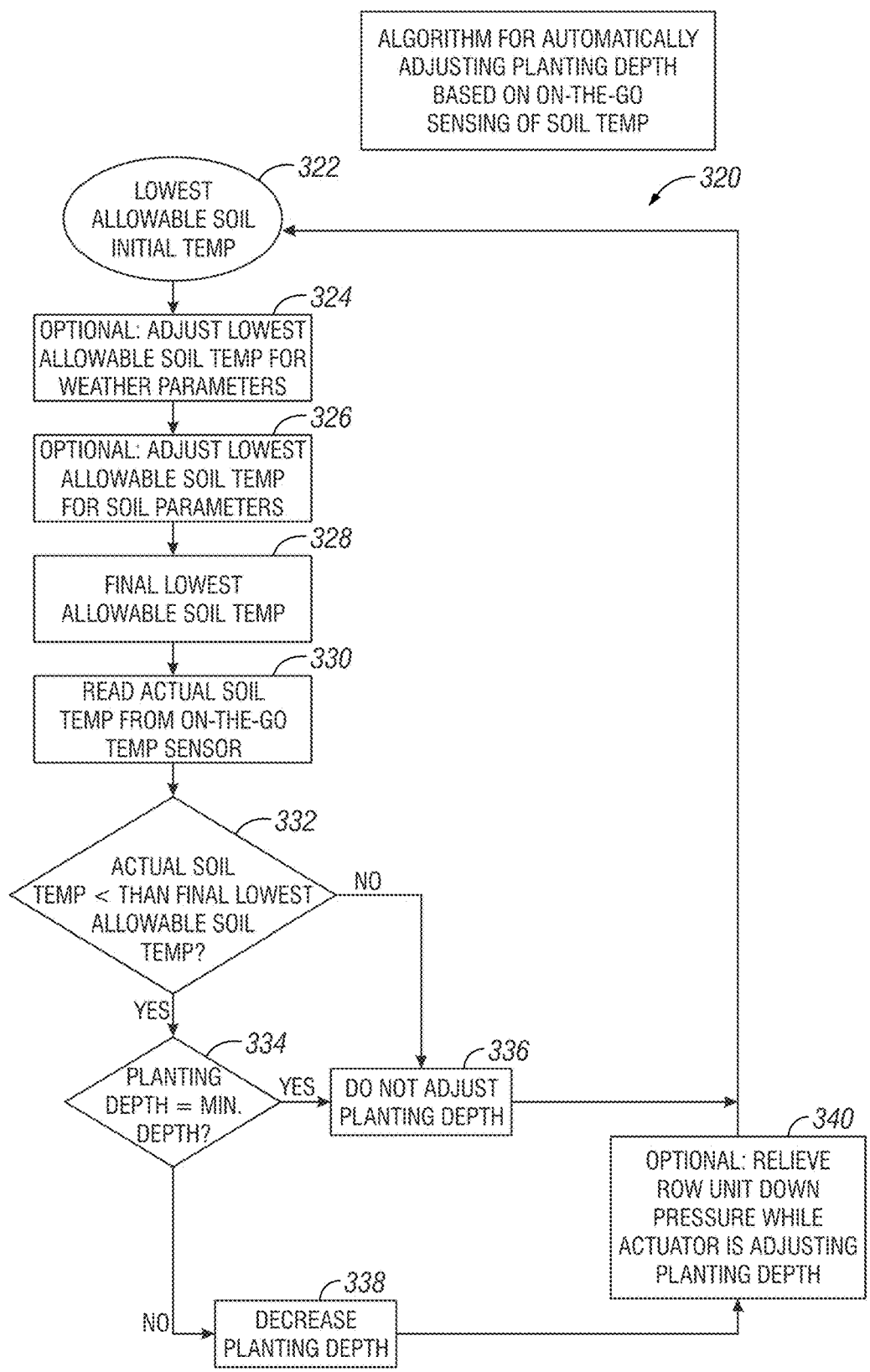
FIG. 11 is a method for automatically adjusting planting depth based on an on-the-go sensing of soil temperature.

FIG. 11 is a method 320 for automatically adjusting planting depth based on an on-the-go sensing of soil temperature. As shown there is a lowest allowable soil initial temperature setting 322. In step 324, an optional step of adjusting the lowest allowable soil temperature for weather parameters may be performed. In step 326, an optional step of adjusting the lowest allowable temperature for soil parameters may be performed. Where adjustments are made in steps 324 or 326, the adjustments may be made according to models, equations, or lookup tables or otherwise. In step 328, there is a final lowest allowable soil temperature obtained after any adjustments. In step 330, an actual soil temperature from the on-the-go temperature sensor is read. In step 332 a determination is made as to whether the actual soil temperature is less than the final lowest allowable soil temperature. If it is, then in step 334 a determination is made as to whether the planting depth is at the minimum depth. If it is not, then in step 338 the planting depth is decreased. If the planting depth is at the minimum depth, then in step 336, it is not adjusted. There is also an optional step 340 of relieving the row unit down pressure while the actuator is adjusting the planting depth.

Figure 12:
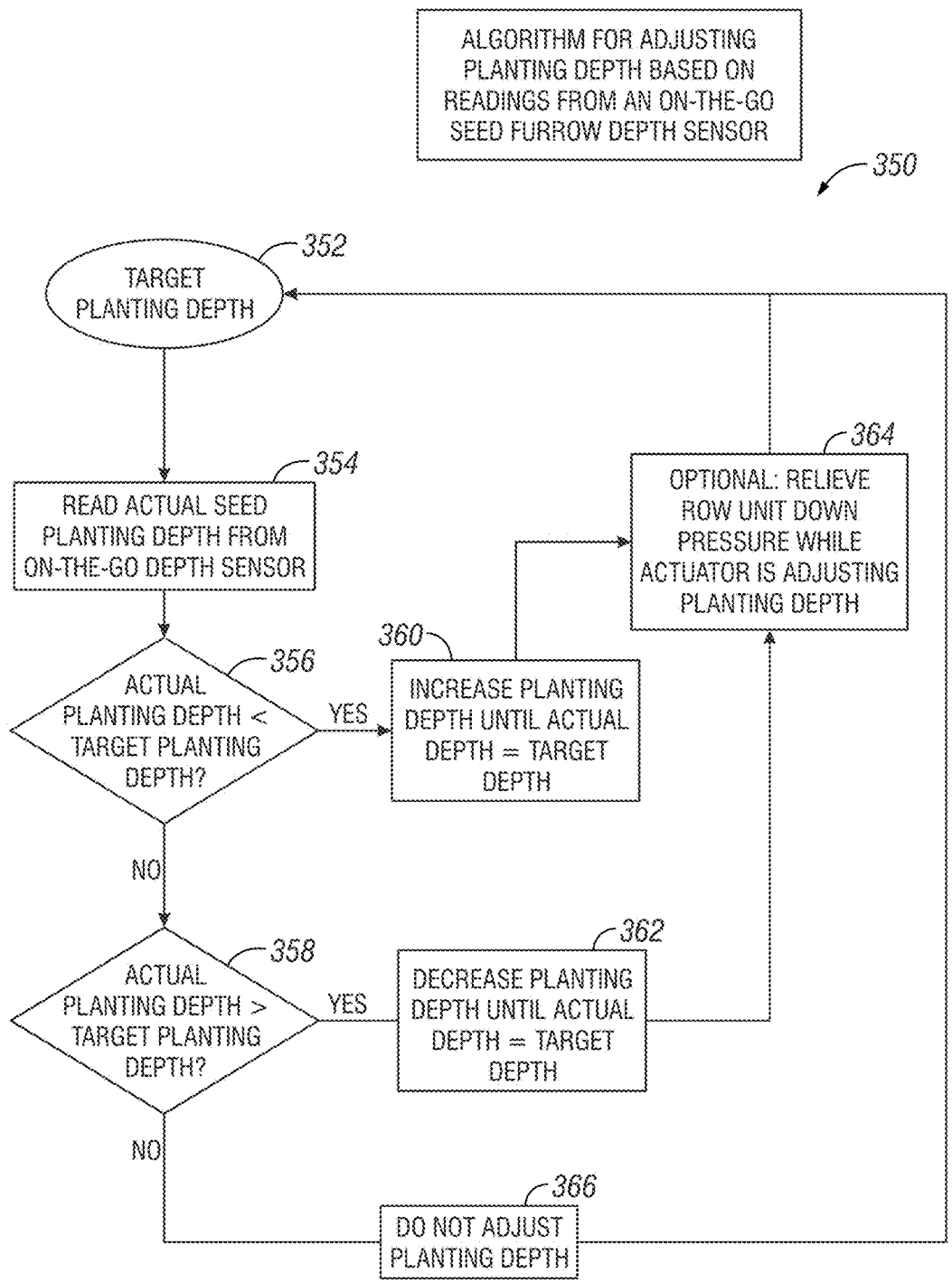
FIG. 12 is a method for adjusting planting depth based on readings from an on-the-go seed furrow depth sensor.

FIG. 12 is a method 350 for adjusting planting depth based on readings from an on-the-go seed furrow depth sensor. As shown, there is a target planting depth 352. In step 354 actual seed planting depth is read from the on-the-go depth sensor. In step 356 a determination is made as to whether the actual planting depth is less than the target planting depth. If it is, then in step 360, the planting depth is increased until the actual depth is equal to the target depth. If not, then in step 358, a determination is made as to whether the actual planting depth is greater than the target planting depth. If it is, then in step 362 the planting depth is decreased until the actual depth is equal to the target depth. If not, then in step 366 the planting depth is not adjusted. Also, as shown there is an optional step 364 that provides for relieving the row unit down pressure while the actuator is adjusting planting depth.

Figure 13:
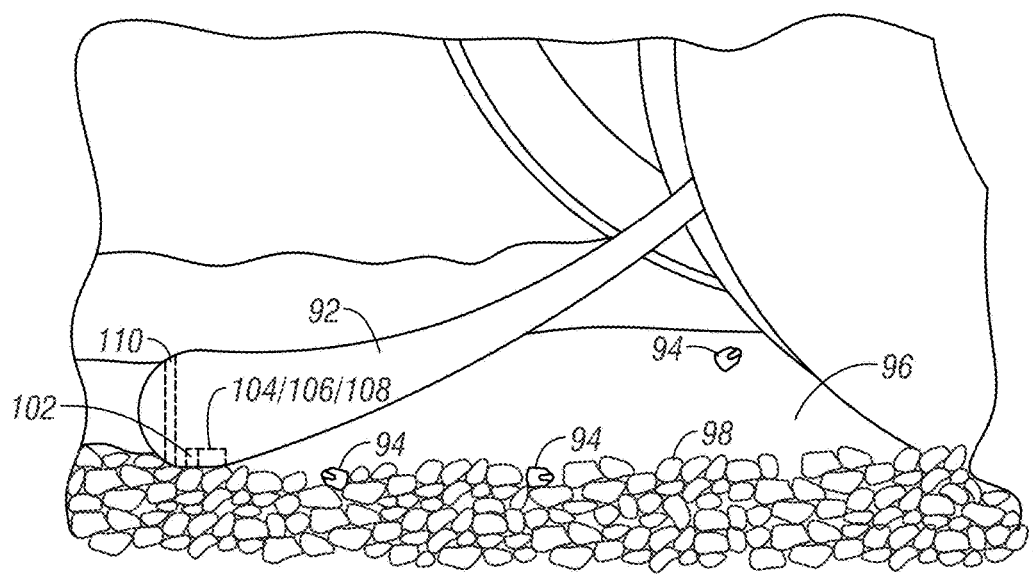

FIG. 13 is a diagram of another example of a seed-firm with one or more sensors built-in. As shown, there are voids in soil at the bottom of the seed trench. There is a seed firmer 92 which may be present on each row unit of a planter in order to improve seed to soil contact. Seed to soil contact sensors and/or soil moisture sensors or other sensors may be incorporated into the base, sides, or base and sides of the seed firmer 92. As shown in FIG. 8, a soil contact sensor 104 is shown, as is a soil temperature sensor 102, a seed count sensor 106, a soil moisture sensor 108, and a depth sensor 110. The seed firmer 92 improves seed to soil contact by pushing the seed 94 firmly into the bottom 98 of a seed trench 96 created by a planter when planting. Where the voids are present in the soil at the bottom of the seed trench, there would be the risk of planting the seeds too deep without using the sensors to take into account depth and soil contact.

Although the invention has been described and illustrated with respect to preferred embodiments thereof, it is not to be so limited since changes and modifications may be made therein which are within the full intended scope of the invention. For example, the present invention contemplates variations in the type of soil moisture sensors utilized, whether it be dielectric or optical. Various structure differences in planter types are also within the full intended scope of the invention such as the number of row units, varying row spacing, split rows, and vacuum, brush-type or finger pickup seed metering systems. Moreover, the order and steps of the methods of the present invention may also be modified or revised in accordance with the changing parameters of the landscape and weather patterns while planting. Furthermore, although algorithms are provided to show how data collected from the sensors may be used, the present invention contemplates that different algorithms may be used applying different logic for control.

What is claimed is:

1. A method of monitoring and displaying readings associated with a sensor measuring cutting depth of a seed trench on a seeder as the seeder seeds a field, the method comprising:

providing a sensor mounted on a seed firmer of the seeder by incorporation into a base, side, or base and sides of the seed firmer;

sensing cutting depth with the sensor on the seeder as the seeder seeds the field comprising measuring height of a seed furrow sidewall of the seed trench; and displaying on a display associated with the seeder a representation of cutting depth of the seed trench.

2. The method of claim 1 wherein the representation of the cutting depth provides a linear distance dimension.

3. The method of claim 1 wherein the representation of the cutting depth comprises a range indicator format.

4. The method of claim 1 wherein the sensing cutting depth with the sensor provides for distinguishing between plant residue on top of ground and soil and wherein the plant residue on the top of the ground is not included in the cutting depth.

5. An apparatus for monitoring and displaying readings associated with a sensor measuring cutting depth of a seed trench on a seeder as the seeder seeds a field, the apparatus comprising:

a seeder implement;

a seed firmer on the seeder implement;

a sensor mounted on the seed firmer by incorporation into a base, side, or base and sides of the seed firmer and measures height of a seed furrow sidewall of the seed trench; and a display associated with the seeder adapted to display a representation of cutting depth of the seed trench based on the sensor.

6. The apparatus of claim 5 wherein the sensor comprises a dielectric or optical sensor for detecting depth of the trench by measuring height of a seed furrow sidewall for distinguishing between plant residue on top of ground and soil and wherein the plant residue on the top of the ground is not included in the cutting depth.

* * * * *